US010517483B2

(12) United States Patent
Wood et al.

(10) Patent No.: US 10,517,483 B2
(45) Date of Patent: Dec. 31, 2019

(54) SYSTEM FOR DETECTING FLUORESCENCE AND PROJECTING A REPRESENTATIVE IMAGE

(71) Applicants: Fred Wood, Medford, NY (US); Dmitry Yavid, Stony Brook, NY (US); Joe Zott, Menlo Park, CA (US); Ron Goldman, Cold Spring Harbor, NY (US)

(72) Inventors: Fred Wood, Medford, NY (US); Dmitry Yavid, Stony Brook, NY (US); Joe Zott, Menlo Park, CA (US); Ron Goldman, Cold Spring Harbor, NY (US)

(73) Assignee: AccuVein, INC., Cold Spring Harbor, NY (US)

( * ) Notice: Subject to any disclaimer, the term of this patent is extended or adjusted under 35 U.S.C. 154(b) by 471 days.

(21) Appl. No.: 14/097,313

(22) Filed: Dec. 5, 2013

(65) Prior Publication Data

US 2014/0187931 A1    Jul. 3, 2014

Related U.S. Application Data

(60) Provisional application No. 61/733,535, filed on Dec. 5, 2012, provisional application No. 61/830,225, filed on Jun. 3, 2013.

(51) Int. Cl.
  *A61B 5/00* (2006.01)
  *A61B 18/20* (2006.01)
  *A61B 18/00* (2006.01)

(52) U.S. Cl.
  CPC .......... *A61B 5/0071* (2013.01); *A61B 5/0077* (2013.01); *A61B 18/20* (2013.01); *A61B 5/742* (2013.01); *A61B 2018/00577* (2013.01)

(58) Field of Classification Search
  None
  See application file for complete search history.

(56) References Cited

U.S. PATENT DOCUMENTS

| 3,136,310 A | 6/1964 | Meltzer |
| 3,349,762 A | 10/1967 | Kapany |

(Continued)

FOREIGN PATENT DOCUMENTS

| FR | 2289149 | 5/1976 |
| GB | 1298707 | 12/1972 |

(Continued)

OTHER PUBLICATIONS

Wu et al., "Three-dimensional imaging of objects embedded in turbid media with fluorescence and Raman spectroscopy", Applied Optics, vol. 34, No. 18, Jun. 20, 1995.*

(Continued)

*Primary Examiner* — Joseph M Santos Rodriguez
(74) *Attorney, Agent, or Firm* — Thomas A. O'Rourke; Bodner + O'Rourke, LLP

(57) ABSTRACT

A fluorescence imaging device detects fluorescence in parts of the visible and invisible spectrum, and projects the fluorescence image directly on the human body, as well as on a monitor, with improved sensitivity, video frame rate and depth of focus, and enhanced capabilities of detecting distribution and properties of multiple fluorophores. Direct projection of three-dimensional visible representations of florescence on three-dimensional body areas advantageously permits viewing of it during surgical procedures, including during cancer removal, reconstructive surgery and wound care, etc. A NIR laser and a human visible laser (HVL) are aligned coaxially and scanned over the operating field of view. When the NIR laser passes over the area where the florescent dye is present, it energizes the dye which emits at a shifted NIR frequency detected by a photo diode. The HVL (Continued)

is turned on when emission is detected, providing visual indication of those positions.

51 Claims, 12 Drawing Sheets

(56) References Cited

U.S. PATENT DOCUMENTS

| | | | |
|---|---|---|---|
| 3,511,227 A | 5/1970 | Johnson |
| 3,527,932 A | 9/1970 | Thomas |
| 3,818,129 A | 6/1974 | Yamamoto |
| 3,984,629 A | 10/1976 | Gorog |
| 4,030,209 A | 6/1977 | Dreidling |
| 4,057,784 A | 11/1977 | Tafoya |
| 4,109,647 A | 8/1978 | Stern |
| 4,162,405 A | 7/1979 | Chance |
| 4,182,322 A | 1/1980 | Miller |
| 4,185,808 A | 1/1980 | Donohoe et al. |
| 4,213,678 A | 7/1980 | Pomerantzeff |
| 4,265,227 A | 5/1981 | Ruge |
| 4,312,357 A | 1/1982 | Andersson et al. |
| 4,315,318 A | 2/1982 | Kato |
| 4,321,930 A | 3/1982 | Jobsis et al. |
| 4,393,366 A | 7/1983 | Hill |
| 4,495,949 A | 1/1985 | Stoller |
| 4,502,075 A | 2/1985 | DeForest et al. |
| 4,510,938 A | 4/1985 | Jobsis |
| 4,536,790 A | 8/1985 | Kruger |
| 4,565,968 A | 1/1986 | Macovski |
| 4,567,896 A | 2/1986 | Barnea |
| 4,576,175 A | 3/1986 | Epstein |
| 4,586,190 A | 4/1986 | Tsuji |
| 4,590,948 A | 5/1986 | Nilsson |
| 4,596,254 A | 6/1986 | Adrian |
| 4,619,249 A | 10/1986 | Landry |
| 4,669,467 A | 6/1987 | Willet |
| 4,697,147 A | 9/1987 | Moran |
| 4,699,149 A | 10/1987 | Rice |
| 4,703,758 A | 11/1987 | Omura |
| 4,766,299 A | 8/1988 | Tierney et al. |
| 4,771,308 A | 9/1988 | Tejima et al. |
| 4,780,919 A | 11/1988 | Harrison |
| 4,799,103 A | 1/1989 | Mucherheide |
| 4,817,622 A | 4/1989 | Pennypacker et al. |
| 4,846,183 A | 7/1989 | Martin |
| 4,862,894 A | 9/1989 | Fujii |
| 4,899,756 A | 2/1990 | Sonek |
| 4,901,019 A | 2/1990 | Wedeen |
| 4,926,867 A | 5/1990 | Kanda |
| RE33,234 E | 6/1990 | Landry |
| 5,074,642 A | 12/1991 | Hicks |
| 5,088,493 A | 2/1992 | Giannini |
| 5,103,497 A | 4/1992 | Hicks |
| 5,146,923 A | 9/1992 | Dhawan |
| 5,174,298 A | 12/1992 | Dolfi |
| 5,184,188 A | 2/1993 | Bull |
| 5,214,458 A | 5/1993 | Kanai |
| 5,222,495 A | 6/1993 | Clarke |
| 5,261,581 A | 11/1993 | Harden |
| 5,293,873 A | 3/1994 | Fang |
| 5,339,817 A | 8/1994 | Nilsson |
| 5,371,347 A | 12/1994 | Plesko |
| 5,406,070 A | 4/1995 | Edgar et al. |
| 5,418,546 A | 5/1995 | Nakagakiuchi et al. |
| 5,423,091 A | 6/1995 | Lange |
| 5,436,655 A | 7/1995 | Hiyama |
| 5,455,157 A | 8/1995 | Adachi |
| D362,910 S | 10/1995 | Creaghan |
| 5,485,530 A | 1/1996 | Lakowicz |
| 5,487,740 A | 1/1996 | Sulek |
| 5,494,032 A | 2/1996 | Robinson |
| 5,497,769 A | 3/1996 | Gratton |
| 5,504,316 A | 4/1996 | Bridgelall et al. |
| 5,519,208 A | 5/1996 | Esparza et al. |
| 5,541,820 A | 7/1996 | McLaughlin |
| 5,542,421 A | 8/1996 | Erdman |
| 5,598,842 A | 2/1997 | Ishihara et al. |
| 5,603,328 A | 2/1997 | Zucker et al. |
| 5,608,210 A | 3/1997 | Esparza et al. |
| 5,610,387 A | 3/1997 | Bard et al. |
| 5,625,458 A | 4/1997 | Alfano |
| 5,631,976 A | 5/1997 | Bolle et al. |
| 5,655,530 A | 8/1997 | Messerschmidt |
| 5,678,555 A | 10/1997 | O'Connell |
| 5,716,796 A | 2/1998 | Bull |
| 5,719,399 A | 2/1998 | Alfano et al. |
| 5,747,789 A | 5/1998 | Godik |
| 5,756,981 A | 5/1998 | Roustaei et al. |
| 5,758,650 A | 6/1998 | Miller |
| 5,772,593 A * | 6/1998 | Hakamata ............... A61B 19/52 348/77 |
| 5,787,185 A | 7/1998 | Clayden |
| 5,814,040 A | 9/1998 | Nelson |
| 5,836,877 A | 11/1998 | Zavislan |
| 5,847,394 A | 12/1998 | Alfano et al. |
| 5,860,967 A | 1/1999 | Zavislan et al. |
| 5,865,828 A * | 2/1999 | Jeng ..................... A61B 18/203 606/11 |
| 5,929,443 A | 7/1999 | Alfano et al. |
| 5,946,220 A | 8/1999 | Lemelson |
| 5,947,906 A | 9/1999 | Dawson, Jr. et al. |
| 5,966,204 A | 10/1999 | Abe |
| 5,969,754 A | 10/1999 | Zeman |
| 5,982,553 A | 11/1999 | Bloom et al. |
| 5,988,817 A | 11/1999 | Mizushima et al. |
| 5,995,856 A | 11/1999 | Manheimer et al. |
| 5,995,866 A | 11/1999 | Lemelson |
| 6,006,126 A | 12/1999 | Cosman |
| 6,032,070 A | 2/2000 | Flock et al. |
| 6,056,692 A | 5/2000 | Schwartz |
| 6,061,583 A | 5/2000 | Shihara et al. |
| 6,083,486 A | 7/2000 | Weissleder |
| 6,101,036 A | 8/2000 | Bloom |
| 6,122,042 A | 9/2000 | Wunderman |
| 6,132,379 A | 10/2000 | Patacsil |
| 6,135,599 A | 10/2000 | Fang |
| 6,141,985 A | 11/2000 | Cluzeau et al. |
| 6,142,650 A | 11/2000 | Brown et al. |
| 6,149,644 A | 11/2000 | Xie |
| 6,171,301 B1 | 1/2001 | Nelson |
| 6,178,340 B1 | 1/2001 | Svetliza |
| 6,230,046 B1 | 5/2001 | Crane et al. |
| 6,240,309 B1 | 5/2001 | Yamashita |
| 6,251,073 B1 | 6/2001 | Imran et al. |
| 6,263,227 B1 | 7/2001 | Boggett et al. |
| 6,272,376 B1 | 8/2001 | Marcu |
| 6,301,375 B1 | 10/2001 | Choi |
| 6,305,804 B1 | 10/2001 | Rice |
| 6,314,311 B1 | 11/2001 | Williams et al. |
| 6,334,850 B1 | 1/2002 | Amano et al. |
| 6,353,753 B1 | 3/2002 | Flock |
| 6,424,858 B1 | 7/2002 | Williams |
| 6,436,655 B1 | 8/2002 | Bull |
| 6,438,396 B1 | 8/2002 | Cook et al. |
| 6,463,309 B1 | 10/2002 | Ilia |
| 6,464,646 B1 | 10/2002 | Shalom et al. |
| 6,523,955 B1 | 2/2003 | Eberl |
| 6,542,246 B1 | 4/2003 | Toida |
| 6,556,854 B1 | 4/2003 | Sato et al. |
| 6,556,858 B1 * | 4/2003 | Zeman ................. A61B 5/0059 250/330 |
| 6,599,247 B1 | 7/2003 | Stetten |
| 6,631,286 B2 | 10/2003 | Pfeiffer |
| 6,648,227 B2 | 11/2003 | Swartz et al. |
| 6,650,916 B2 | 11/2003 | Cook et al. |
| 6,689,075 B2 | 2/2004 | West |
| 6,690,964 B2 | 2/2004 | Bieger et al. |
| 6,702,749 B2 | 3/2004 | Paladini et al. |
| 6,719,257 B1 | 4/2004 | Greene et al. |
| 6,755,789 B2 | 6/2004 | Stringer |
| 6,777,199 B2 | 8/2004 | Bull |
| 6,782,161 B2 | 9/2004 | Barolet et al. |
| 6,845,190 B1 | 1/2005 | Smithwick |
| 6,882,875 B1 | 4/2005 | Crowley |

(56) References Cited

U.S. PATENT DOCUMENTS

| | | |
|---|---|---|
| 6,889,075 B2 | 5/2005 | Marchitto et al. |
| 6,913,202 B2 | 7/2005 | Tsikos et al. |
| 6,923,762 B1 | 8/2005 | Creaghan |
| 6,980,852 B2 | 12/2005 | Jersey-Wiluhn et al. |
| 7,092,087 B2 | 8/2006 | Kumar |
| 7,113,817 B1 | 9/2006 | Winchester |
| 7,158,660 B2 | 1/2007 | Gee et al. |
| 7,158,859 B2 | 1/2007 | Wang |
| 7,225,005 B2 | 5/2007 | Kaufman et al. |
| 7,227,611 B2 | 6/2007 | Hull et al. |
| 7,239,909 B2 | 7/2007 | Zeman |
| 7,247,832 B2 | 7/2007 | Webb |
| 7,283,181 B2 | 10/2007 | Allen |
| 7,302,174 B2 | 11/2007 | Tan et al. |
| 7,333,213 B2 | 2/2008 | Kempe |
| D566,283 S | 4/2008 | Brafford et al. |
| 7,359,531 B2 | 4/2008 | Endoh et al. |
| 7,376,456 B2 | 5/2008 | Marshik-Geurts |
| 7,431,695 B1 | 10/2008 | Creaghan |
| 7,488,468 B1 | 2/2009 | Miwa |
| 7,532,746 B2 | 5/2009 | Marcotte et al. |
| 7,545,837 B2 | 6/2009 | Oka |
| 7,559,895 B2 | 7/2009 | Stetten |
| 7,579,592 B2 | 8/2009 | Kaushal |
| 7,608,057 B2 | 10/2009 | Woehr et al. |
| 7,708,695 B2 | 5/2010 | Akkermans |
| 7,792,334 B2 | 9/2010 | Cohen |
| 7,848,103 B2 | 12/2010 | Cannon |
| 7,904,138 B2 | 3/2011 | Ustuner |
| 7,904,139 B2 | 3/2011 | Chance |
| 7,925,332 B2 | 4/2011 | Crane et al. |
| 7,966,051 B2 | 6/2011 | Xie |
| 8,032,205 B2 | 10/2011 | Mullani |
| 8,078,263 B2 | 12/2011 | Zeman et al. |
| 8,187,189 B2 | 5/2012 | Jung et al. |
| 8,199,189 B2 | 6/2012 | Kagenow et al. |
| 8,320,998 B2 | 11/2012 | Sato |
| 8,336,839 B2 | 12/2012 | Timoszyk et al. |
| 8,364,246 B2 | 1/2013 | Thierman |
| 8,480,662 B2 | 7/2013 | Stolen |
| 8,494,616 B2 | 7/2013 | Zeman |
| 8,498,694 B2 | 7/2013 | McGuire, Jr. et al. |
| 8,509,495 B2 | 8/2013 | Xu et al. |
| 8,537,203 B2 | 9/2013 | Seibel |
| 8,548,572 B2 | 10/2013 | Crane et al. |
| 8,630,465 B2 | 1/2014 | Wieringa |
| 8,649,848 B2 | 2/2014 | Crane et al. |
| 2001/0006426 A1 | 7/2001 | Son |
| 2001/0055462 A1* | 12/2001 | Seibel ............... A61B 1/00048 |
| | | 385/147 |
| 2001/0056237 A1 | 12/2001 | Cane |
| 2002/0016533 A1* | 2/2002 | Marchitto ........... A61B 5/0066 |
| | | 600/310 |
| 2002/0118338 A1 | 8/2002 | Kohayakawa |
| 2002/0188203 A1 | 12/2002 | Smith |
| 2003/0018271 A1 | 1/2003 | Kimble |
| 2003/0052105 A1 | 3/2003 | Nagano |
| 2003/0120154 A1 | 6/2003 | Sauer |
| 2003/0125629 A1 | 7/2003 | Ustuner |
| 2003/0156260 A1 | 8/2003 | Putilin |
| 2004/0015062 A1 | 1/2004 | Ntziachristos |
| 2004/0015158 A1 | 1/2004 | Chen et al. |
| 2004/0022421 A1 | 2/2004 | Endoh et al. |
| 2004/0046031 A1 | 3/2004 | Knowles et al. |
| 2004/0237051 A1 | 8/2004 | Ogawa et al. |
| 2004/0171923 A1 | 9/2004 | Kalafut et al. |
| 2004/0222301 A1 | 11/2004 | Willins et al. |
| 2005/0017924 A1 | 1/2005 | Utt et al. |
| 2005/0033145 A1 | 2/2005 | Graham et al. |
| 2005/0043596 A1 | 2/2005 | Chance |
| 2005/0047134 A1 | 3/2005 | Mueller et al. |
| 2005/0085732 A1 | 4/2005 | Sevick-Muraca |
| 2005/0085802 A1 | 4/2005 | Gruzdev |
| 2005/0113650 A1 | 5/2005 | Pacione et al. |
| 2005/0131291 A1 | 6/2005 | Floyd et al. |
| 2005/0135102 A1 | 6/2005 | Gardiner et al. |
| 2005/0141069 A1 | 6/2005 | Wood et al. |
| 2005/0143662 A1 | 6/2005 | Marchitto et al. |
| 2005/0146765 A1 | 7/2005 | Turner |
| 2005/0154303 A1 | 7/2005 | Walker |
| 2005/0157939 A1 | 7/2005 | Arsenault et al. |
| 2005/0161051 A1 | 7/2005 | Pankratov et al. |
| 2005/0168980 A1 | 8/2005 | Dryden et al. |
| 2005/0174777 A1 | 8/2005 | Cooper et al. |
| 2005/0175048 A1 | 8/2005 | Stern et al. |
| 2005/0187477 A1 | 8/2005 | Serov |
| 2005/0215875 A1 | 9/2005 | Khou |
| 2005/0265586 A1 | 12/2005 | Rowe et al. |
| 2005/0281445 A1 | 12/2005 | Marcotte et al. |
| 2006/0007134 A1* | 1/2006 | Ting ..................... G06F 3/0386 |
| | | 345/156 |
| 2006/0020212 A1 | 1/2006 | Xu |
| 2006/0025679 A1 | 2/2006 | Viswanathan et al. |
| 2006/0052690 A1 | 3/2006 | Sirohey et al. |
| 2006/0081252 A1 | 4/2006 | Wood |
| 2006/0100523 A1 | 5/2006 | Ogle |
| 2006/0103811 A1 | 5/2006 | May et al. |
| 2006/0122515 A1 | 6/2006 | Zeman |
| 2006/0129037 A1 | 6/2006 | Kaufman et al. |
| 2006/0129038 A1 | 6/2006 | Zelenchuk et al. |
| 2006/0151449 A1 | 7/2006 | Warner |
| 2006/0173351 A1 | 8/2006 | Marcotte et al. |
| 2006/0184040 A1 | 8/2006 | Keller et al. |
| 2006/0206027 A1 | 9/2006 | Malone |
| 2006/0232660 A1 | 10/2006 | Nakajima et al. |
| 2006/0253010 A1 | 11/2006 | Brady et al. |
| 2006/0271028 A1 | 11/2006 | Altshuler et al. |
| 2007/0016079 A1 | 1/2007 | Freeman et al. |
| 2007/0070302 A1 | 3/2007 | Govorkov |
| 2007/0115435 A1 | 5/2007 | Rosendaal |
| 2007/0176851 A1 | 8/2007 | Wiley |
| 2007/0238957 A1 | 10/2007 | Yared |
| 2008/0004525 A1* | 1/2008 | Goldman ............. A61B 5/0059 |
| | | 600/425 |
| 2008/0004533 A1* | 1/2008 | Jansen et al. ........ A61B 5/0059 |
| | | 600/476 |
| 2008/0021329 A1* | 1/2008 | Wood .................. A61B 5/0059 |
| | | 600/476 |
| 2008/0045841 A1 | 2/2008 | Wood et al. |
| 2008/0147147 A1 | 6/2008 | Griffiths et al. |
| 2008/0177184 A1* | 7/2008 | Goldman ............. A61B 5/0059 |
| | | 600/476 |
| 2008/0194930 A1 | 8/2008 | Harris et al. |
| 2008/0214940 A1 | 9/2008 | Benaron |
| 2008/0281172 A1* | 11/2008 | Thurston ............. A61B 5/0059 |
| | | 600/317 |
| 2008/0281208 A1* | 11/2008 | Thurston ............. A61B 5/0059 |
| | | 600/477 |
| 2009/0018414 A1 | 1/2009 | Toofan |
| 2009/0054767 A1* | 2/2009 | Telischak ............ A61B 5/0071 |
| | | 600/431 |
| 2009/0082629 A1 | 3/2009 | Dotan |
| 2009/0171205 A1 | 7/2009 | Kharin |
| 2010/0051808 A1 | 3/2010 | Zeman et al. |
| 2010/0061598 A1 | 3/2010 | Seo |
| 2010/0087787 A1 | 4/2010 | Woehr et al. |
| 2010/0177184 A1 | 7/2010 | Berryhill et al. |
| 2010/0312120 A1 | 12/2010 | Meier |
| 2011/0092965 A1* | 4/2011 | Slatkine ............. A61F 9/00802 |
| | | 606/5 |
| 2011/0112407 A1* | 5/2011 | Wood .................. A61B 5/0059 |
| | | 600/476 |
| 2011/0125028 A1* | 5/2011 | Wood .................. A61B 5/0064 |
| | | 600/476 |
| 2011/0275932 A1 | 11/2011 | LeBlond |
| 2013/0147916 A1 | 6/2013 | Bennett |
| 2014/0039309 A1 | 2/2014 | Harris et al. |

(56) References Cited

U.S. PATENT DOCUMENTS

| | | |
|---|---|---|
| 2014/0046291 A1 | 2/2014 | Harris et al. |
| 2014/0194747 A1 | 7/2014 | Kruglick |

FOREIGN PATENT DOCUMENTS

| | | |
|---|---|---|
| GB | 1507329 | 4/1978 |
| JP | S60-108043 A | 6/1985 |
| JP | 04-042944 | 2/1992 |
| JP | 07-255847 | 10/1995 |
| JP | 08023501 A | 1/1996 |
| JP | 08-164123 | 6/1996 |
| JP | 2000/316866 A | 11/2000 |
| JP | 2002 328428 A | 11/2002 |
| JP | 2002/345953 A | 12/2002 |
| JP | 2004 237051 | 8/2004 |
| JP | 2004/329786 A | 11/2004 |
| KR | 2003/0020152 A | 3/2003 |
| WO | WO 1994 22370 | 10/1994 |
| WO | WO 96/39925 | 12/1996 |
| WO | WO 1996 39925 | 12/1996 |
| WO | WO 9826583 | 6/1998 |
| WO | WO 99/48420 | 9/1999 |
| WO | WO 2001 82786 | 11/2001 |
| WO | WO 2003 009750 | 2/2003 |
| WO | WO 2005053773 | 6/2005 |
| WO | WO 2007078447 | 7/2007 |

OTHER PUBLICATIONS

Wiklof, Chris, "Display Technology Spawns Laser Camera," LaserFocusWorld, Dec. 1, 2004, vol. 40, Issue 12, PennWell Corp., USA.

Nikbin, Darius, "IPMS Targets Colour Laser Projectors," Optics & Laser Europe, Mar. 2006, Issue 137, p. 11.

http://sciencegeekgirl.wordpress.com/category/science-myths/page/2/ Myth 7: Blood is Blue.

http://www.exploratorium.edu/sports/hnds_up/hands6.html "Hands up! To Do & Notice: Getting the Feel of Your Hand".

http://www.wikihow.com/See-Blood-Veins-in-Your-Hand-With-a-Flashlight "How to See Blood Veins in Your Hand With a Flashlight".

Thermo Scientific, Fluorescent Probes, available at: www.piercenet.com/browse.cfm?fldID=4DD9D52E-5056-8A76-4E6E-E217FAD0D86B.

Perkin Elmer, Targeted Fluorescent Imaging Agents, available at: www.perkinelmer.com/catalog/category/id/Targeted.

"Mayo Clinic Finds Early Success with Laser That Destroys Tumors with Heat," available at: www.mayoclinic.org/news2010-jax/6006.html.

\* cited by examiner

SYSTEM FOR DETECTING FLUORESCENCE AND PROJECTING A REPRESENTATIVE IMAGE

CROSS REFERENCE TO RELATED APPLICATIONS

This application claims priority on U.S. Provisional Application Ser. No. 61/733,535 filed on Dec. 5, 2012, and claims priority on U.S. Provisional Application Ser. No. 61/830,225, filed on Jun. 3, 2013, with the disclosures of each incorporated herein by reference.

FIELD OF INVENTION

This invention is related to the field of fluorescent medical imaging.

BACKGROUND OF INVENTION

Fluorescence is a phenomenon of light emission by a substance that has previously absorbed light of a different wavelength. In most cases, the emitted light has a longer wavelength, and therefore lower energy, than the absorbed light. However, when the absorbed electromagnetic radiation is intense, it is possible for one atom or molecule to absorb two photons; this two-photon absorption can lead to emission of radiation having a shorter wavelength than the absorbed radiation. Fluorescent light can be easily separated from reflected excitation light, thus providing excellent selectivity in applications where fluorescent light may carry some useful information about the substances and structures which emitted it.

This property is particularly important in various medical imaging applications, where fluorescent light may be emitted by fluorescent dyes, also known as fluorophores, with affinity to certain biological materials such as blood, or dyes conjugated to biological markers with specific affinity to certain tissues, proteins or DNA segments, and can be a reliable proxy for imaging internal body structures, such as blood vessels, lymph nodes, etc., as well as finding signs of disease, such as necrosis or cancer.

Usually, fluorescent biological markers are introduced externally, specifically with a purpose of binding to and imaging specific organs and tissues. In some cases, they are naturally-occurring, which is known as biological auto-fluorescence.

Most fluorescent substances, whether biological or not, have specific absorption and emission spectra, with peaks at certain wavelength. Sometimes, more than one peak may be present in either absorption or emission spectrum, or both. In any case, any fluorescent imaging system must provide excitation light at one wavelength and detect the emission light at different wavelength. Since the optical efficiency of fluorescence is usually quite low, emission light is usually much weaker than excitation light. Hence, optical filters which accept emission light and block excitation light are also usually present in a fluorescent imaging system.

Of particular interest are the fluorescent dyes which both absorb and emit light in the Near Infrared (NIR) part of the spectrum, approximately from 700 to 1000 nm wavelength. Within this band, human tissues are particularly transparent, so the fluorescent dyes may be seen at most depths and images may be of particular clarity.

Fluorescent medical imaging systems are known in prior art, including those designed for detection of NIR fluorescent dyes.

Usually, fluorescent images are combined with conventional, reflected-light images and presented to a medical practitioner on a common monitor, so the distribution of the fluorescent die can be visible in its surroundings. Since the NIR fluorescent image is outside of the human visible light range, it is usually mapped to a human visible color and displayed on a monitor superimposed on top of the captured color image of the biological object of interest. The system can display either still or moving images. A medical practitioner can use such a system to detect, for example, cancer cells during surgery, detect perfusion during reconstructive surgery, and detect the location of lymph nodes. During open surgery, wherein the surgeon is directly viewing the field of surgery, utilization of a monitor is disadvantageous in the surgeon must glance away from the surgical site to view the image of the fluorescence. Upon returning to view the surgical area, the surgeon must estimate the position of the florescence based upon his memory of the display on the monitor. Alternative, the surgeon can perform the required work while directly viewing the monitor as opposed to directly viewing the surgical area. This approach is disadvantaged in that it is cumbersome to operate without directly viewing the surgical site. Further, when viewing the monitor the surgeon losses all three dimensional information that is normally obtained when directly viewing the surgical area.

While being valuable surgical and diagnostic tools, known fluorescent cameras suffer from a number of limitations, mostly stemming from very low signal levels produced by fluorescent dyes. Those limitations are insufficient sensitivity, low video frame rates or long integration time necessary for taking a still image, as well as a limited depth of focus, especially if a large objective lens is used to alleviate sensitivity problems.

There are many known fluorescent dyes and or molecules that are used in the medical field, also referred to florescent probes or fluorescent markers. (see, Thermo Scientific, Fluorescent Probes, available at: www.piercenet.com/browse.cfm?fldID=4DD9D52E-5056-8A76-4E6E-E217FAD0D86B, the disclosures of which are hereby incorporated by reference).

Furthermore, in the following article, near-infrared fluorescence nanoparticle-base probes for use in imaging of cancer are described and is hereby incorporated by reference: He, X., Wang, K. and Cheng, Z. (2010), "In vivo near-infrared fluorescence imaging of cancer with nanoparticle-based probes," WIREs Nanomed Nanobiotechnol, 2: 349-366. doi: 10.1002/wnan.85.

OBJECTS OF THE INVENTION

It is an object of this invention to visualize fluorescence which is invisible to the human eye, either because it is outside of visible wavelength range, or because it is too weak to be seen by a naked eye, by re-projection directly onto human tissue on a surgical or diagnostic site and thus free the medical practitioner from shifting his sight from patient to monitor and back It is another object of this invention to alleviate the deficiencies of existing fluorescent cameras and increase the sensitivity, the video frame rates and the depth of focus.

It is yet another object of this invention to enable a fluorescent camera to detect the presence of multiple fluorophores with distinct spectra in human tissues and adequately convey the information about their presence and distribution to the medical practitioner.

It is yet another object of this invention to detect temporal changes in fluorophore distribution and convey this information to the medical practitioner.

It is yet another object of this invention to enable detection of fluorescence life time of a fluorophore, which might convey additional clinically-relevant information about fluorophore distribution and interaction with surrounding tissues. It may also help to distinguish between fluorophores with the same spectra but different life time.

It is also an object of this invention to extract information about the depth of the fluorophore deposit in the human body, thus enabling 3-dimensional fluorescence imaging.

And it is also an object of this invention to improve the performance of fluorescence imaging in endoscopic applications.

Further objects and advantages of the invention will become apparent from the following description and claims, and from the accompanying drawings.

SUMMARY OF THE INVENTION

In this application a fluorescence imaging device is described which is capable of detecting fluorescence in visible and invisible parts of the spectrum and projecting the fluorescence image directly on the human body, as well as on the monitor, with improved sensitivity, video frame rate and depth of focus and enhanced capabilities of detecting distribution and properties of multiple fluorophores.

Projecting the visible representation of the florescence directly on the human body has the significant advantage of allowing the surgeon to view the florescence directly on the patient while performing the surgery. Since the parts of the body being operated on are three dimensional, the viewing by the surgeon of the projected visible image thereon is therefore inherently three dimensional, providing an advantage to the surgeon.

An illustrative example where the present invention would be useful is open surgery for cancer removal. It is known that injecting a patient with fluorescent dyes conjugated with specific biological markers will cause the dyes to accumulate in cancer cells. With the present invention, during open surgery the surgeon can simply aim the device at the surgical area and all of the cancer cells will appear to be visually glowing due to the selective projection of the visible laser on the surgical area. In this manner the surgeon can make certain to only remove the cancerous materials, and can insure that all the cancerous cells are appropriately removed.

A further illustrative field is the area of reconstructive surgery and wound care. In these cases insuring that there is appropriate blood flow into parts of the body is critical. In this instance, during the reconstructive surgery the fluorescent dyes can be injected into the patients' blood stream and the device used to show the blood flow to the newly constructed area. By projecting directly onto the reconstructed area an image of the blood flow, the surgeon can insure in real time that the flow is appropriate to provide appropriate healing.

In one embodiment, the system includes a NIR laser for energizing the florescent dye, for example Indocyanine green (ICG). Also included is a human visible laser (i.e., a laser emitting light at a wavelength that is visible to the human eye) for displaying the areas where the florescence is detected. Both the NIR and the visible laser are aligned co axially and scanned over the operating field of view. When the NIR laser passes over the area where the florescent dye is present, the dye emits at a shifted NIR frequency which is detected by a photo diode. Based upon the position of the NIR laser when the emission is detected, the position of the florescent dye is identified. The human visible laser is then turned on at positions corresponding to the position of the florescent dye, thereby providing a visual indication of the position of the florescent dye.

DETAILED DESCRIPTION OF THE INVENTION

Figure 1:
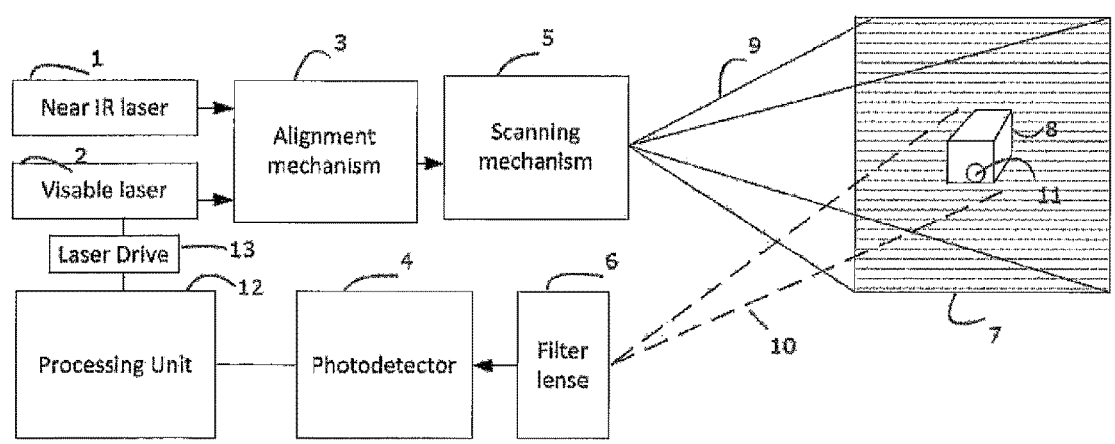
FIG. 1—this block diagram describes a fluorescence imaging device capable of re-projecting fluorescence image directly on the human body.

FIG. 1 shows a block diagram of a fluorescence imaging device capable of re-projecting fluorescence image directly on the human body, for example, during a surgery. A florescent dye, such as HER2Sense or RediJect 2-DG 750, which is available from Perkin Elmer in Waltham, Mass. (see, Perkin Elmer, Targeted Fluorescent Imaging Agents, available at: www.perkinelmer.com/catalog/category/id/Targeted), is delivered to the surgical area, via sub-cutaneous or intra-venous injection and accumulates in the objects of interest, for example cancer cells 11 of the patient.

A near IR laser 1 is provided at an IR frequency that is suitable for exciting the florescent dye in the cancer cells 11 of the surgical area. The near IR laser 1 passes through an alignment mechanism 3 which co axially aligns the near IR laser 1 with a visible laser 2. As a specific illustrative example, the near IR laser 1 could be a semiconductor laser diode which emits at 780 nm wavelength and the visible laser 2 can be a red laser that emits at a 640 nm wavelength. The coaxially aligned lasers beams are then delivered to a scanning mechanism 5 which moves them in a raster pattern along a field of view 9 aimed upon the surgical area 7.

When the near IR laser passes over the cancer cells 11 the florescent dye contained therein is energized and emits light in a band roughly centered around an 820 nm wavelength. The emitted light travels along detection path 10 to a filter lens 6. The filter lens 6 has optical characteristics that allow the 820 nm wavelength light traveling along detection path 10 to pass through the filter lens 6, and is focused by the filter lens 6 onto photodetector 4. The filter lens 6 also has optical characteristics that block the 780 nm near IR laser light from passing through to the photodetector 4. The photodetector 4 converts the 820 nm light emitting from the cancer cells 11 into an analog signal which is then provided processing unit 12.

In one embodiment, called the real-time mode, the processing unit 12 drives in real time a laser drive 13, which in turn turns on and off the visible laser 2 so that the visible laser 2 represents the amount of the 820 nm wavelength light falling upon the photodetector 4. In this manner, the visible laser 2 is transmitted onto the surgical area 7 thereby illuminating with visible light the locations where the fluorescent dye is present.

In another embodiment, called an image capture mode, the processing unit 12 stores a time sequence output of the photodetector 4 into a memory location. In this manner, an entire image frame representing the 820 nm fluorescence in the field of view 9 is stored in the memory location. Image processing can be performed on the memory location to enhance and augment the captured image. The processing unit 12 then outputs a time sequence output to the laser drive 13 such that the visible laser outputs the entire frame stored in the memory location. In this matter, the frame captured in the memory location is transmitted onto the surgical area thereby illuminating the visible light at the locations where the fluorescent dye is present. In this image capture mode, the output frame from the visible laser 2 is delayed in time from the image frame stored by the processing unit 12. The device of FIG. 1 can be contained in handheld devices or can be mounted on a stand. In the handheld device, provided the frame rate is adequately fast, for example, 60-100 frames per second, this delay will not result in noticeable jitter.

Figure 2:
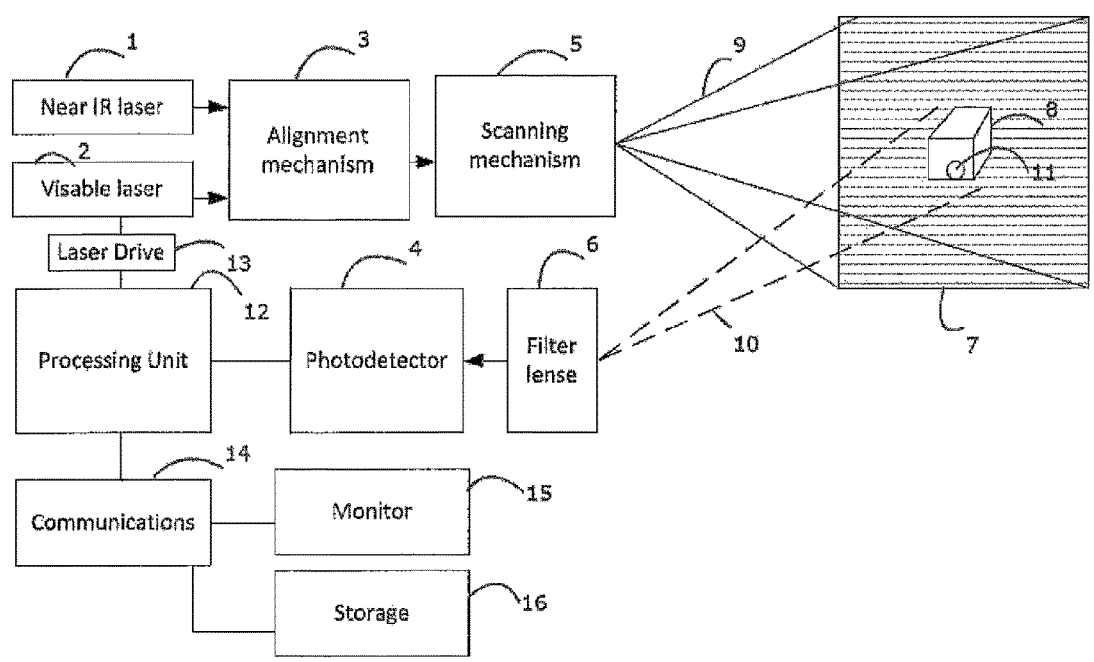
FIG. 2—this block diagram describes a fluorescence imaging device capable of re-projecting fluorescence image directly on the human body and on a monitor.

A further embodiment of the device of FIG. 1 is shown in FIG. 2. The elements 1-13 function in the image capture mode as described in reference to FIG. 1. Further, the processing unit 12 communicates the frame image stored in the memory representative of the 820 nm fluorescence in the field of view 9 through communications 14 circuitry to either a monitor 15 or storage 16 device, or to both the monitor 15 and the storage 16 device. The monitor 15 displays the frame image of the fluorescence in the field of view 9. Further, the storage 16 device, such as, for example, a hard drive, solid state memory device or computer, can store the frame image and later recall the image for viewing on the monitor 15 or for archiving the frame images.

The user of the FIG. 2 embodiment will have the ability to view a visual image of the 820 nm fluorescence in the field of view 9 generated by the visible laser 2 and scanned by the scanning mechanism 5 directly on the surgical area 7. Surgical area 7 often has a three-dimensional geometry, and the visible image is displayed on all portions of the three-dimensional geometry of the surgical area facing the direction of the scanning mechanism. Further, the user can view the visual image of the 820 nm fluorescence in the field of view 9 directly on the monitor 15. The display on the monitor can be digitally amplified or reduced to fit the user's needs.

Figure 3:
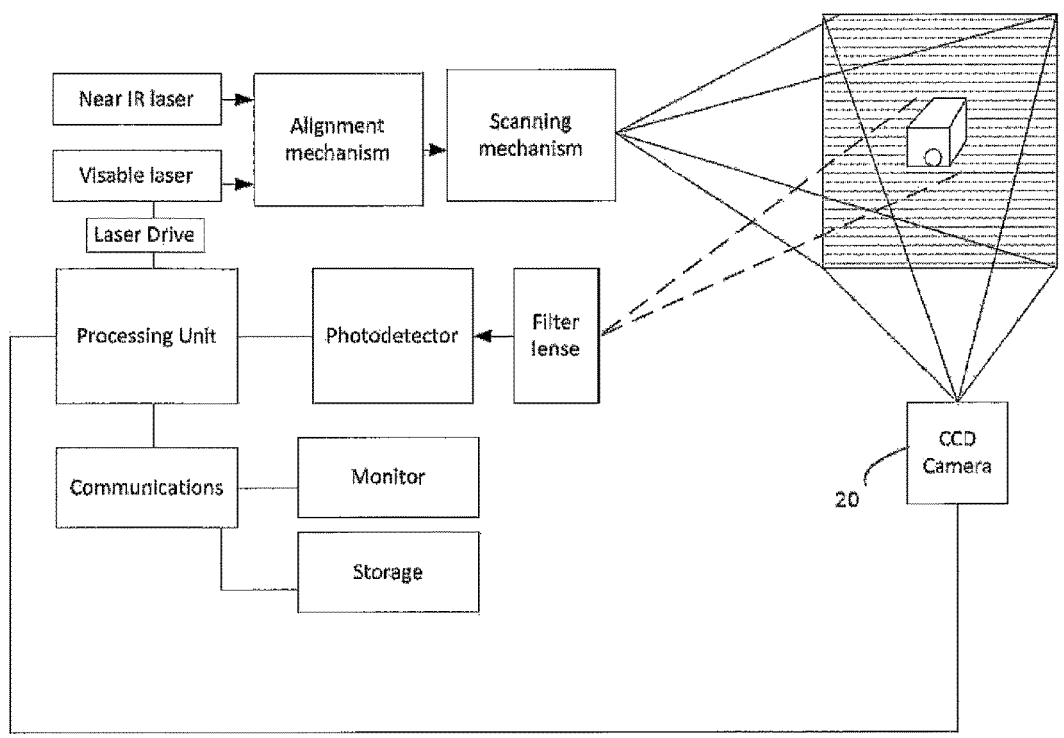
FIG. 3—this block diagram describes a fluorescence imaging device capable of re-projecting fluorescence image directly on the human body, overlap the fluorescent image on the visible image from a CCD camera and display the combined image on a monitor.

Another embodiment of the present invention is shown on FIG. 3. All the elements are the same as FIG. 2; however, a CCD Camera 20 has been electrically connected to the processing unit 12. While the invention of FIG. 2 is operating, the CCD camera 20 takes a color image of the surgical field 7. Accordingly, the CCD camera captures an image of the surgical field 7 while the visible laser 2 is projecting a visible representation of where the florescent material is. In this manner, the CCD camera 20 captures and communicates to the processing unit 12 an image representation of both the color image of the surgical field 7 together with the projected representation of the fluorescence. Such combined image can then be displayed on the monitor. In order to display just the visible image, without the fluorescence the near IR laser can be temporarily turned off thereby stopping the fluorescing and thereby the CCD camera images just the visible image.

The projected visible image captured by camera can also be analyzed by the processing unit in order to provide the most accurate alignment of the projected image on curved surfaces of the body with the captured fluorescent image.

Figure 4:
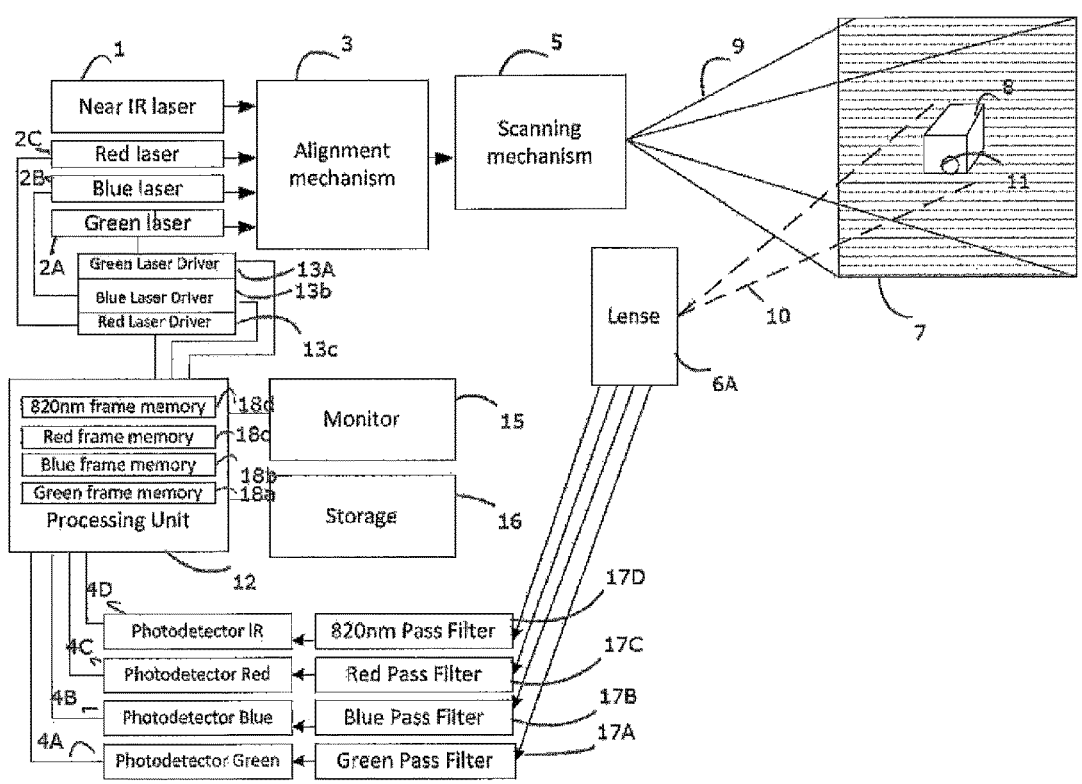
FIG. 4—this block diagram describes a fluorescence imaging device capable of re-projecting fluorescence image directly on the human body using full RGB colors, overlap the fluorescent image on the visible image from a full-color laser scanning camera and display the combined image on a monitor.

A further embodiment of the present invention is shown in FIG. 4 wherein a color representation of the surgical area 7 is captured together with the fluorescent representation of the surgical area 7.

Within a surgical field a surgical area is treated with a florescent dye, the florescent dye accumulates in, for example, the cancer cells 11 of the patient. The florescent dye can be injected into the blood stream of the patient or can be locally injected near the suspect cancer cells 11.

A near IR laser 1 is provided at an IR frequency that is suitable for exciting the florescent dye in the cancer cells 11 of the surgical area. The near IR laser 1 passes through an alignment mechanism 3 which co axially aligns the near IR laser 1 with a green laser 2A, a blue laser 2B and a red laser 2C. As an specific illustrative example, the near IR laser 1 could be a semiconductor laser diode which emits at 780 nm wavelength, the visible red laser 2C can be a 640 nm semiconductor red laser; the visible blue laser 2B can be a 440 nm semiconductor blue laser, and the visible green laser 2A can be a can be a laser emitting in the a 510 to 540 nm range. The coaxially aligned lasers are then provided to a scanning mechanism 5 which move the coaxially aligned laser beams in a raster pattern along a field of view 9 aimed upon the surgical area 7.

When the near IR laser passes over the cancer cells 11 in the surgical area 7, the florescent dye contained therein is energized and emits light in a band roughly centered around an 820 nm wavelength. The emitted 820 nm wavelength light travels along detection path 10 to a lens 6A. The lens 6A has optical characteristics to focus the 820 nm wavelength light traveling along detection path 10 onto photodetector IR 4D. A 820 nm pass filter 17D is provided which allows the 820 nm wavelength to pass while rejecting visible light reflected off the surgical area 7 from the red laser 2C, the green laser 2A and the blue laser 2B laser as well as rejecting the Near IR light from reflecting off the surgical area from the near IR laser 1. The 820 nm pass filter 17D is positioned between the lens 6A and the Photodetector IR 4D. In this manner the photodetector IR 4D receives only the 820 nm fluorescent emission from the surgical area 7 and converts the 820 nm light emitting within the surgical area 7 into an analog signal which is then provided processing unit 12. The processing unit 12 converts the analog signal from photodetector IR 4d into a digital signal which is stored on a frame by frame basis in 820 nm frame memory 18d When the green laser 2A, blue laser 2B and Red laser 2C passes over the surgical area 7 within the field of view 9, the visible color characteristics of the surgical area 7 are reflected to varying degrees depending upon the visible color of the surgical area 7. The reflected light travels along detection path 10 to a lens 6A. The lens 6A has optical characteristics to focus the reflected green laser 2A, blue laser 2B and red laser 2C light traveling along detection path 10 onto each of photodetectors 4A-4C, respectively. A green pass filter 17A, a blue pass filter 17B and a red pass filter 17C, which allows only their respective colors of visible light to pass through, are positioned between the lens 6A and the respective photodetectors 4A-4C. In this manner each of the respective photodetectors 4A-4C receives only one of the three reflected colors, and each photodetector 4A-4C converts the respective light into analog signals which are then provided to processing unit 12. The processing unit 12 converts the analog signal from the respective photodetectors 4a-4c into a digital signal which is stored on a frame by frame basis in green frame memory 18a, blue frame memory 18b and red frame memory 18c, respectively.

In this manner, an entire frame representing the 820 nm fluorescence in the field of view 9 together with a color image of the surgical area 7 within the field of view 9 is stored within frame memory 18a-18d of the processing unit 12. To directly illuminate the areas within the surgical area 7 that emitted the 820 nm light, the 820 nm frame memory 18d is mapped to a selected color for projection onto the surgical area 7. For example, if a red color is selected as the display color, the processing unit 12 outputs a time sequence of the frame within the 820 nm frame memory to the red laser drive 13c such that the red laser 2c is driven to output onto the surgical area the image stored within the 820 nm frame memory. Accordingly, the surgeon will see directly on the surgical area 7 the red laser projection at the locations where the 820 nm fluorescence occurred. While in the present embodiment, the red laser 2C was utilized for projecting the visible image onto the surgical area 7, in alternative embodiments, any desired combination of the red laser 13c, the blue laser 13b and the green laser 13A could be used to project a desired visible color.

In the present embodiment, the image contained in the 820 nm frame buffer can mapped to a visible color and superimposed onto one or more of the green, blue or red frame memories 18a-18c and the resulting modified frame memories 18a-18c are then displayed on monitor 15 and output to storage 16. For example, in an embodiment wherein bright green is selected as the color for displaying on the monitor 15 the image of the fluorescence stored in 820 nm frame memory 18d, then green frame memory 18a is modified based upon the contents of 820 nm frame memory 18d, such that bright green is stored in green frame memory 18a at the locations where the 820 nm frame memory 18d stored indication of florescence detection.

Accordingly, with the present invention the surgeon has two ways of viewing fluorescence within the surgical area 7. In the first, the visible lasers (one or more of the green, blue and red lasers 18a-18c are projected directly on the surgical site and directly locations which are fluorescing. Further, the image of the fluorescing is mapped to a color and display on the monitor 15 together with a color image of the surgical area 7.

In this embodiment, the color lasers 2A-2C are used to illuminate the surgical area 7 to capture a color image, and one or more of the color lasers is used to project the representation of the areas of fluorescence. This can be accomplished by time multiplexing the lasers 2A-2C. For example, every other frame can be allocated for the capture of the color image and the alternate frames can be allocated to displaying via the one or more color lasers 2a-2c the representation of the fluorescence. The net effect will be a white background with the image of the florescence superimposed thereon.

There exists a large number of fluorophores which can be utilized with the present invention. Each fluorophores is activated by particular frequency of light, and emits a particular frequency of light. It is understood that the Near IR laser 1 can be of any frequency sufficient to activate the emissions of the fluorophore, and the 820 nm pass filter 17d and the photodetector IR 4d, can be modified to allow the frequency of light emitted by the fluorophore to be passed and detected. In this manner the present invention is applicable for the wide array of fluorophores. In a still further embodiment, it is possible to utilize two or more fluorophores, having different optical characteristics, at the same time with the surgical area 7, The device of FIG. 4 can be modified so that there are additional lasers incorporated for activating the fluorophores, and additional pass filters and photodetectors for detecting the different frequencies of light, emitted by the fluorophores. Controls can be incorporated to select which lasers should be activated based upon the fluorophores utilized in a procedure. Further, an auto select mode can be implemented where each laser for exciting the fluorophores is momentarily turned on, and only if a reflection is received from the corresponding fluorophores is that channel used in the steady state operation of the device.

Figure 5:
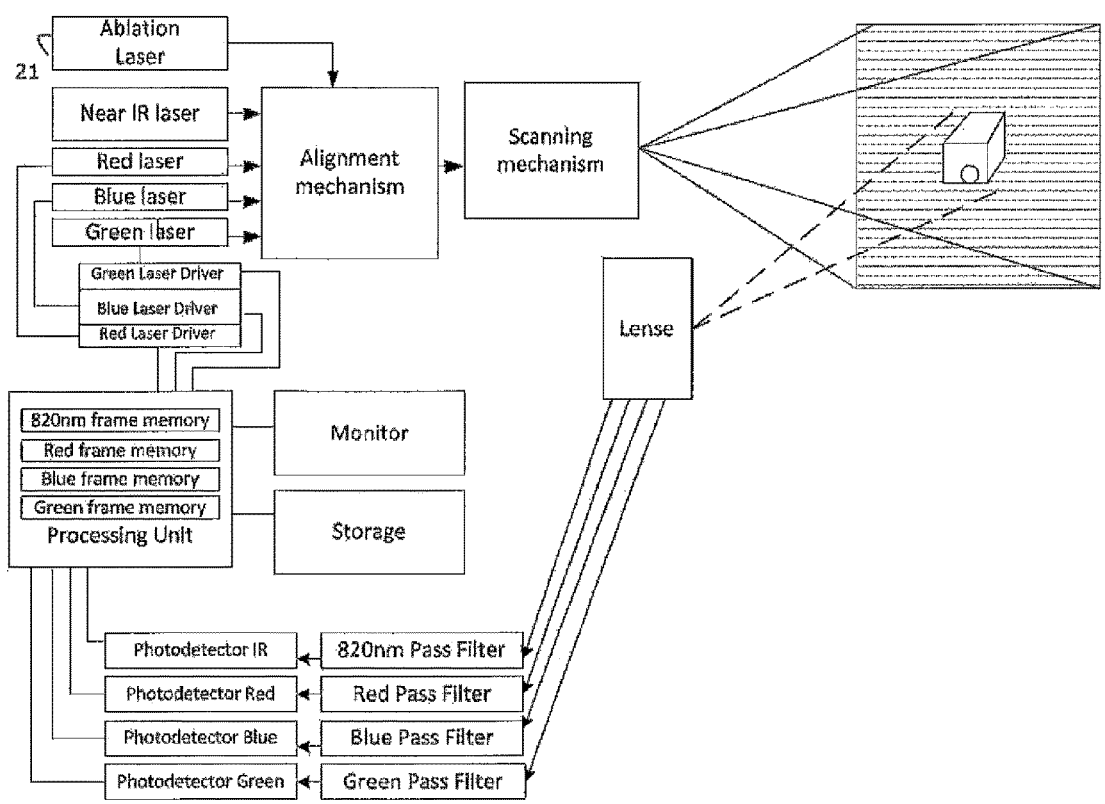
FIG. 5—this block diagram describes a fluorescence imaging device capable of re-projecting fluorescence image directly on the human body using full RGB colors, overlap the fluorescent image on the visible image from a full-color laser scanning camera and display the combined image on a monitor. This device has an additional ablation laser, capable of controlled delivery of laser light to select regions of the human body designated based on the acquired fluorescence image.

FIG. 5 is the same as FIG. 4 with the addition of an ablation laser 21. In an embodiment wherein the florescent dye is introduced to bind to cancer cells 11, in addition to causing the visible light to illuminate cancer cells 11, an ablation laser 21 can be controlled so that it turns on only when the lasers are aimed by the scanning mechanism at the cancer cells.

In an alternative embodiment, the scanning mechanism can particularly be a pointing mirror (as opposed to a resonance mirror). In this manner, the ablation laser 21 can be aimed at the desired cancer location for a prolonged period of time to enable sufficient heating to destroy the cells.

Early success with laser ablation on various types of cancer patients has been achieved at the Mayo Clinic (see, "Mayo Clinic Finds Early Success with Laser That Destroys Tumors with Heat," available at: www.mayoclinic.org/news2010-jax/6006.html). The device of FIG. 5 can be used to more particularly control the aiming of the laser so that it falls only on the desired locations.

Figure 6:
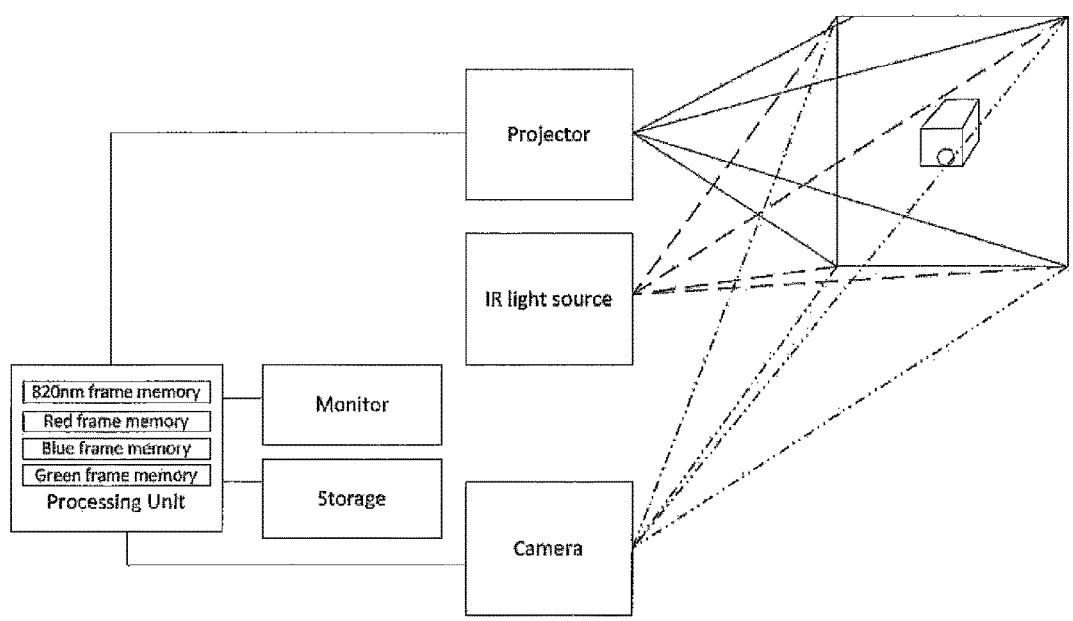
FIG. 6—this block diagram describes a fluorescence imaging device capable of re-projecting fluorescence image directly on the human body, overlap the fluorescent image on the visible image from a CCD camera and display the combined image on a monitor. This device uses an imaging, rather than a laser scanning, projector, such as a Digital Light Processor (DLP) projector.

FIG. 6 is an embodiment wherein a projector (which can be of any type, for example, laser projector, DLP projector, LCD projector, is configured solely for projecting visible light of one or more colors. An IR light source, at a frequency sufficient to cause a fluorophore to emit a different frequency of light, is aimed at the surgical site. The IR light source can either flood the surgical site or can be a scanned light source. A camera is configured to detect a wide frequency range of light, including the visible spectrum and the frequency emitted by the fluorophore. The captured image is stored in a processing unit wherein it is then displayed on a monitor and also could be stored in storage for record keeping. Further the portion of the captured image corresponding to the frequency emitted by the fluorophore, in this case 820 nm, is provided to the projector which in turn projects the image onto the surgical area. Accordingly, a surgeon can see the florescence by either viewing the monitor or directly looking at the surgical area.

Figure 7:
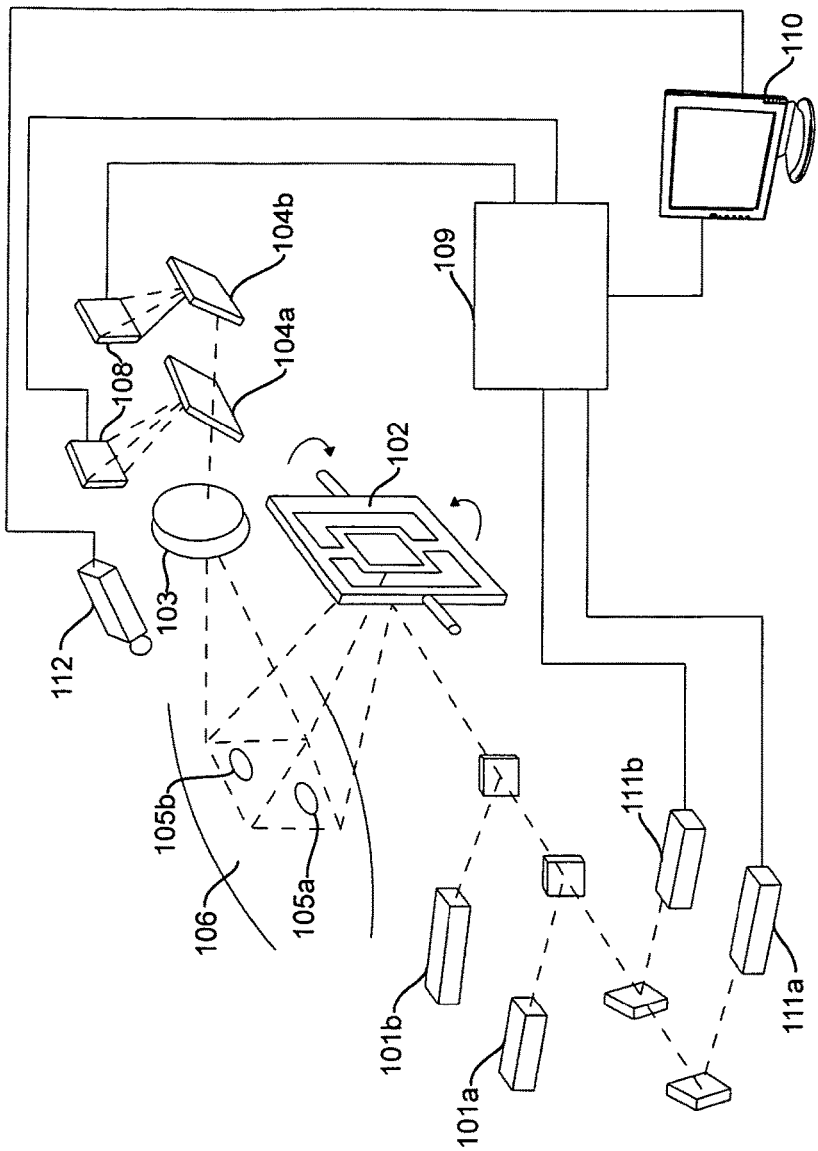
FIG. 7—this drawing shows a simplified layout of the device of FIG. 3.

Embodiments presented on FIG. 1 . . . 6 are further illustrated with a simplified layout of FIG. 7. Light collection system 103 insures that the light emitted by fluorophore particles reaches the light detectors 108. Filters 4 are chosen to correspond to the emission bandwidth of fluorophores 105. Detectors 108 convert light into electrical signals which are processed in electronic block 109, which forms a 2D image corresponding to the distribution of fluorophores in tissue. Said image is presented on the monitor 110.

Some of the detectors 108 and filters 104 may be configured to receive the reflected light from excitation lasers 101 or projection lasers 111 (of which more below), in addition to fluorescence light. That enables the device to act like a camera in IR and/or visible bands. Electronic block 109 may also perform various image-enhancing processing steps, such as integration over multiple frames, contrast enhancing, etc.

In addition to color mapping, the electronic block 109 is also responsible for brightness mapping of certain levels of light emitted by fluorophores to corresponding levels of power of the projection lasers. Such mapping could be linear, single binary threshold, etc. Additionally, the electronic block 109 may produce other video effects to emphasize certain features of the image, such as blinking or periodic color changes.

It is also possible to modulate the brightness of the illumination lasers in accordance with the distribution of light collected from the fluorophore. Applying more illumination where fluorescence is weak and less illumination where it is strong would increase the effective dynamic range of acquired image.

Since the light emitted by fluorophores is usually scant, the corresponding electrical signals are week and susceptible to noise. To optimize image quality, the electronic block may be performing on-the-fly noise estimates and adjust the brightness mapping accordingly. Additionally, the electronic block may tune the bandwidth of the signal processing tract depending on the minimal feature size in the observed fluorescent image.

In clinical practice, it is often important to overlap the image representing fluorescent signature of the tissue with a regular image of the same area. To achieve that, an imaging camera 112 can be employed, looking at the same field of view as the scanner. The camera will pick up both the reflected colors of the tissue and the image re-projected by the projection lasers. Preferably, colors distinct from tissue colors should be chosen for re-projection. It is also beneficial to synchronize the frame rate of the camera with that of the scanner.

Detectors 108 are typically photo-diodes (PD), with appropriate electronic gain down the signal tract. However, in order to improve signal-to-nose (SNR) ratio and facilitate detection of very weak signals, a photo-multiplier tube (PMT) may be used.

Figure 8:
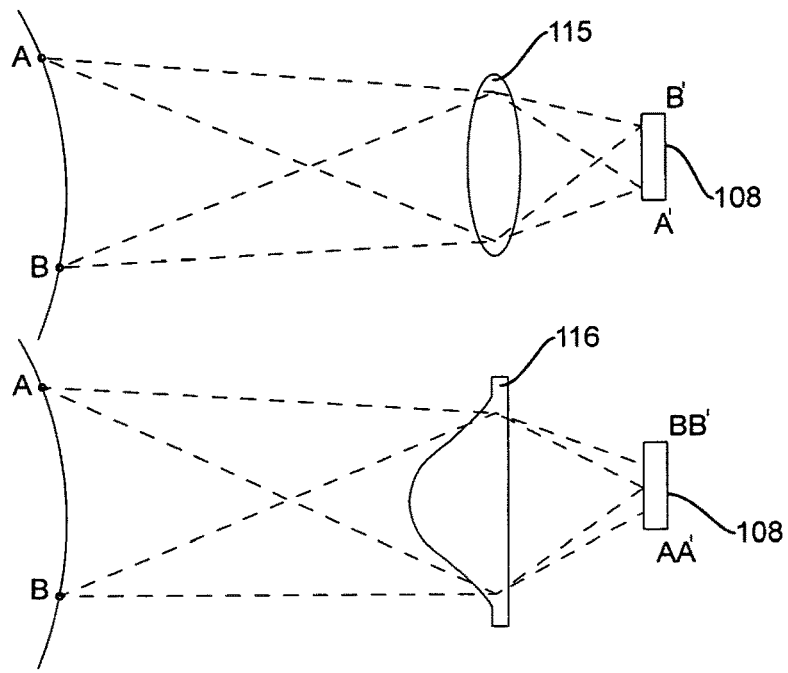
FIG. 8—this drawing shows the difference between the imaging and non-imaging light collection and the advantage of the latter for a fluorescence imaging device.

Also, to improve fluorescent light collection, a non-imaging light collection system can be used, since non-imaging light collectors can be substantially larger than imaging ones. The difference between them is illustrated on FIG. 8. The imaging collection system 115 has the ability to collect light from a point A or B on the target into a point A' or B' on the detector. A non-imaging system 116 can only collect light from a point on the target into a relatively large area (AA' or BB') on the detector, making it unsuitable for use with pixelated sensors. In a scanning device, however, only temporal resolution of the detector matters. Refractive, diffractive or reflective non-imaging collectors may be used.

Figure 9:
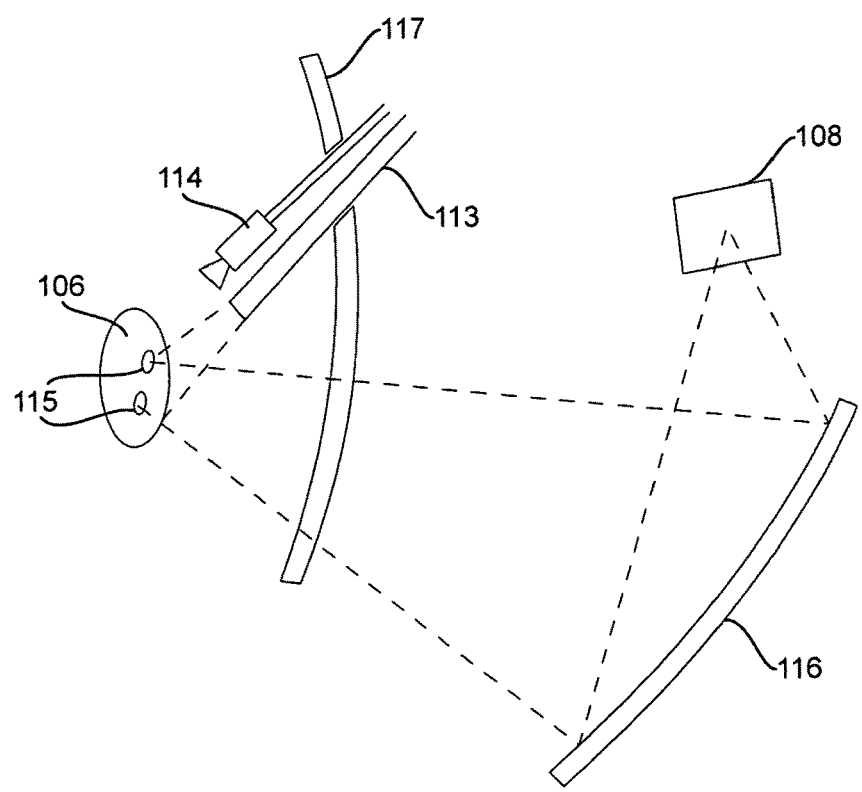
FIG. 9—this drawing shows a simplified layout of an endoscopic fluorescence imaging device.

The use of very large collectors in conjunction with PMT or other high-sensitivity detectors enables imagine of internal tissues, where the scanned raster of the excitation and projection light is delivered through the endoscope 113 (FIG. 9), while the fluorescent light is collected externally, coming through skin 117. A miniature endoscopic camera 114 may still be used to produce a combined image with fluorescent features superimposed over regular optical image. A miniature endoscopic camera in and of itself is typically incapable of picking up weak fluorescent light.

Figure 10:
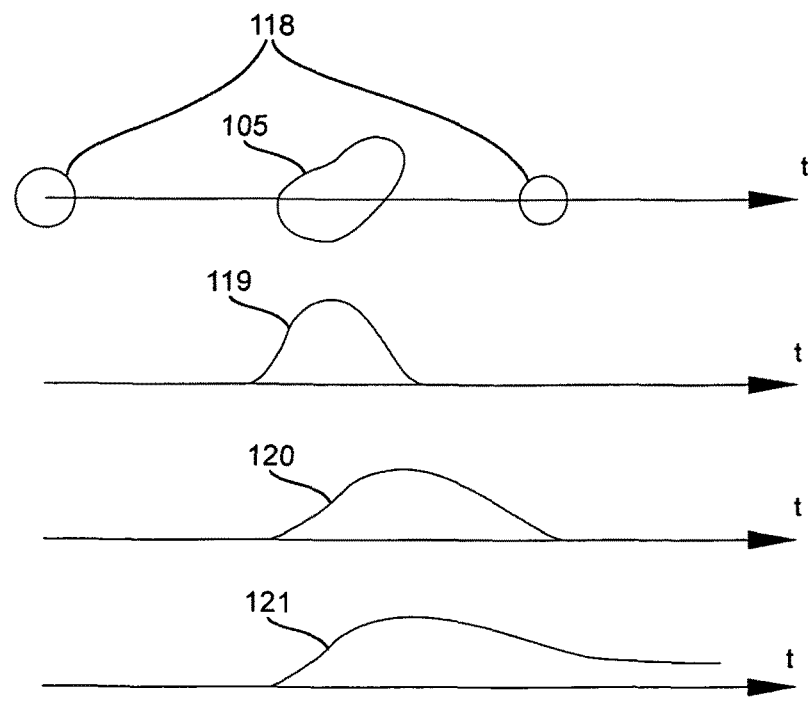
FIG. 10—these graphs show the difference between temporal responses of short and long fluorescent life fluorophores while excited by a laser scanning beam.

Additional advantage of scanning fluorescence detector is its ability to resolve signals in time domain, thus distinguishing between fast- and slow-decaying fluorophores, even if their emission spectra are identical. FIG. 10 shows an excitation laser beam 118 scanning across fluorophore particle 105 and the temporal graphs of excitation light 119 and responses of fast (120) and slow (121) fluorophores. To increase time resolution, the excitation laser itself may be modulated and the temporal response detected synchronously, possibly, with integration across several frames.

It was also disclosed that coupling such a scanning detection device with an imaging camera may be particularly advantageous, as the fluorescent image from the scanner may be superimposed upon the color image from the camera to provide geometrically-accurate, clinically-relevant information not otherwise visible to the surgeon.

Figure 11:
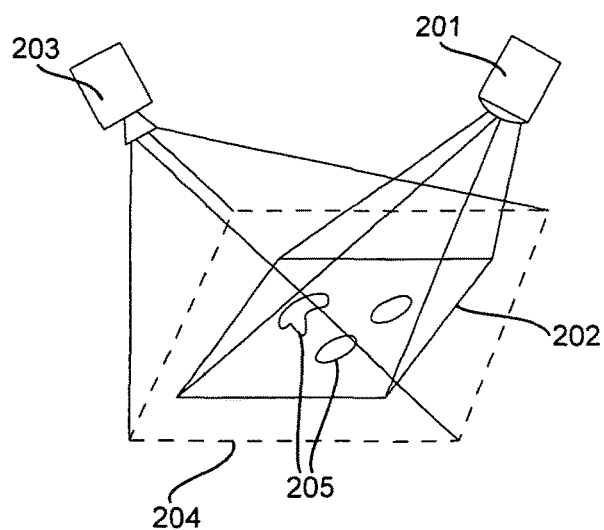
FIG. 11—this drawing shows a simplified optical Field-of-View (FOV) of a fluorescence imaging device.

To realize full benefits of such alignment, it is important to establish the correspondence between data captured by the scanning device 201 and imaging camera 203, (FIG. 11). This is facilitated by projecting a frame 2 around the field of view (FOV) of the scanning device 1, or some other registration elements which are fixed in the FOV, such as corners. For best results, the frame rate of the camera should be synchronized with that of the scanner, via camera's trigger input or other arrangement. Assuming that the entire scanning FOV is contained within the camera FOV 4, the position of such registration elements can be detected by the camera and their coordinates within the camera FOV can be established. Then the coordinates of all other pixels of the scanning device can be found within the camera FOV by interpolation.

If the target surface is not planar, the registration elements may not be able to convey all the information needed for alignment every pixel of both scanner's and camera's images. In this case the entire projected image may be analyzed and used for alignment.

However, inclusion of the projected registration elements, as well as detected fluorescent structures 5, may degrade the quality of the camera image. To avoid that, a camera can capture frames with variable timing and the image processing software may process frames in two streams, as depicted on FIG. 12. In this case "bright" frames 226 are captured while projection frames 223 are active and used for alignment only, while "dark" frames 225 are captured while projection frames 223 are not active and used for fusion with bio-fluorescence data. The exposure of "bright" and "dark" frames may be different. Additionally, partial "bright" frames may be captured during a single camera exposure and subsequently stitched in software. This would have an advantage of capturing more "dark" frames and hence providing fused frames with clinically-relevant information at higher rate, while "bright" frames captured at lower rate may still provide sufficient alignment precision.

Figure 12:
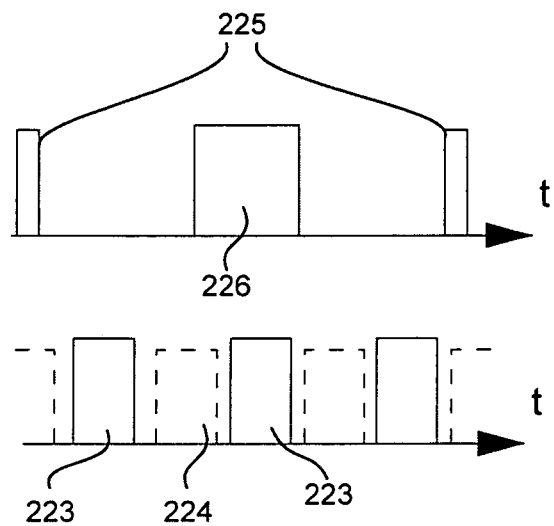
FIG. 12—these timing diagrams illustrate the process of simultaneously acquiring a fluorescent image and projecting with a fluorescence imaging device.

Additionally, still referring to FIG. 12, non-active projection periods 224, during which all lasers of the scanning device are off, can be used to capture so-called "black" frames from the scanning device, i.e. frames which contains no fluorescence data, just noise. The data in those frames may be filtered or otherwise processed, stored, and then subtracted from frames with valid data. While thermal noise and some other forms of noise are non-repeatable and hence cannot be canceled out this way, the ambient light noise and the electronic interference from internal and external sources may be repeatable and hence may be reduced or eliminated by black frame subtraction.

Figure 13:
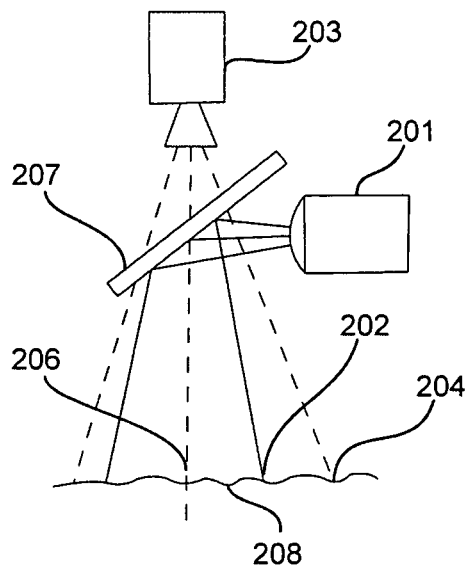
FIG. 13—this drawing shows a method of optically combining the FOV of laser scanner and a CCD camera of a fluorescence imaging device.

The electronic alignment by registration elements as described above may need considerable processing resources. In some cases it may be advantageous to align the scanning device and a camera opto-mechanically, in such a way that their optical axes are co-located along the same line 6 when reaching the target surface 8 (FIG. 13). To achieve this, a coaxial coupling element 207 is employed. Such coupling element may be a dichroic mirror (if the wavelengths used by the scanning device and the camera are sufficiently different), or a polarizing mirror or polarizing cube (if the light used by the scanning device is linearly polarized and the camera can tolerate the loss of half the light), or even a half-mirror (if both the scanning device and the camera can tolerate the loss of some light). Other configurations of the coupling element are possible too.

Figure 14:
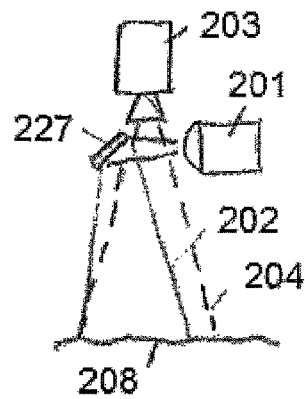
FIG. 14—this drawing shows an alternative method of optically combining the FOV of laser scanner and a CCD camera of a fluorescence imaging device.

If a coaxial coupling element is not feasible, a small coupling mirror 227 placed right outside of the camera FOV may be employed to bring the FOVs of the scanning device and the camera to nearly-coaxial direction (FIG. 14). In this case, some electronic alignment may still be necessary, however, the computational intensity and the precision of such alignment are greatly improved.

Figure 15:
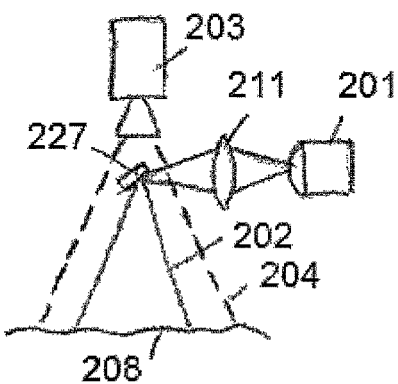
FIG. 15—this drawing shows yet another method of optically combining the FOV of laser scanner and a CCD camera of a fluorescence imaging device.

If mirror 227 is significantly smaller than the camera's aperture, it may be employed within the camera FOV, as per FIG. 15. In this case, it blocks some of the aperture, but the amount of light entering the camera around it may still be sufficient.

It may also be advantageous to employ an additional objective 211, which would create a virtual image of the origin point of the scanner somewhere near the mirror 227, thus reducing the required size of the mirror 227. Similar optical arrangement with an additional objective may be used for the camera as well.

No matter which arrangement is used for the coupling, it is advantageous to co-locate the origin points of the scanning device and the camera, so the relative size of their FOVs stays constant or nearly constant, irrespective of the distance to the target.

While a laser scanning device is capable of re-projecting the collected bio-luminescent information onto the target, it may be advantageous to use a different, non-scanning projector for this purpose. The advantages of non-scanning projectors may include higher light output and lower cost. It is conceivable to use a powerful DLP or LCoS-based non-scanning projector as a replacement of a surgical light, so the projected image will not have to compete with ambient light.

As with cameras, for best results, the frame rate of a projector should be synchronized with that of the seamier.

Figure 16:
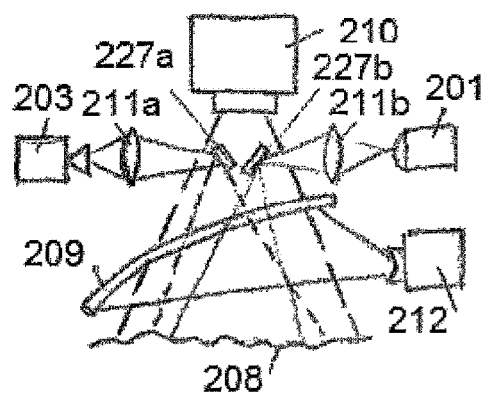
FIG. 16—this drawing shows a method of optically combining the FOV of an imaging projector, such as a DLP projector, and a CCD camera of a fluorescence imaging device.

All of the above-mentioned alignment methods can be used for an imaging projector as well. This is illustrated by an example on FIG. 16, where two coupling mirrors 27a and 27b are placed within the FOV of a projector 10 (most imaging projectors have fairly large apertures). Additional objectives 211a and 211b insure the smallest possible size of coupling mirrors, and hence, low loss of projector's light. A parabolic hot mirror 209 is also shown, collecting the fluorescent light into a detector 212. This arrangement assumes that the fluorescent light has longer wavelength than visible light (emitted by the projector and captured by the camera). Generally, a detector 212 may be collocated with the scanner 201, or be positioned in a different place, as the position of the detector has little impact on device's sensitivity.

Figure 17:
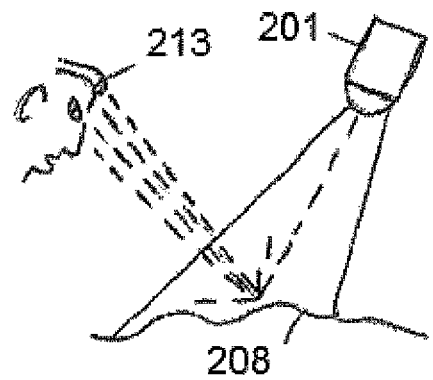
FIG. 17—this drawing shows a fluorescence imaging device with a head-mount sensor for correcting the re-projected image.

The projected light may hit the target surface in such a way that an abnormally large (FIG. 17) or abnormally small amount of light will be reflected toward the User's eyes, due to specular reflection. This problem may be alleviated by a sensor wearable by the User near his/her eyes, which would provide feedback for the projector controller, and thus adjust the amount of light going to each particular pixel of the image according to surface reflectance at that point in the direction of the User.

Figure 18:
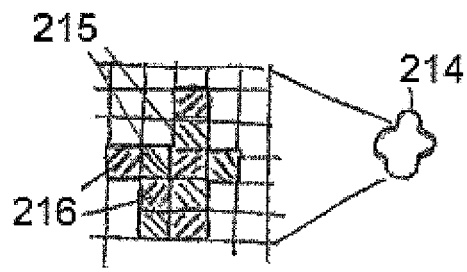
FIG. 18—this diagram illustrates the visual enhancement of re-projected image through synchronized blinking.

The visibility of the projected pattern 214 (FIG. 18), indicating detected fluorescence, may be enhanced, if it is divided into two or more sub-areas, which blink in a synchronized fashion. Left part of FIG. 18 shows a magnified projected pattern 214, which is on the right, where 215 and 216 represent two such sub-areas, designated by different hatching: for example, when areas 215 are lit up, areas 216 remain dark, and vice versa. Areas might be one pixel each, or larger.

Figure 19:
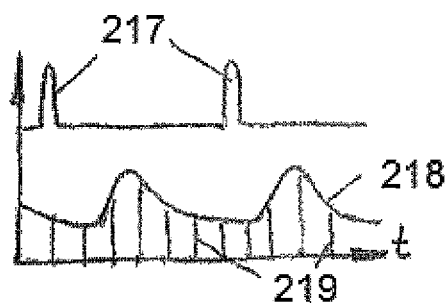
FIG. 19—these timing diagrams illustrate time-resolved fluorescence detection.

A unique property of a scanning bio-fluorescence detection device is its ability to provide time-resolved data. To take advantage of it, the excitation laser should emit pulses 217, their duration being considerably shorter than the duration of a scanning pixel (FIG. 19). The detection system should also be fast enough to be able to take multiple read-outs 219 within a scanning pixel. Then, a temporal response 218 can be measured. This temporal data can be used to assess the fluorophore temporal response, as in Fluorescence-Lifetime Imaging Microscopy (FLIM), or to assess the time of light propagation from the fluorescence source, and hence, the depth of such source, enabling tomographic imaging.

Figure 20:
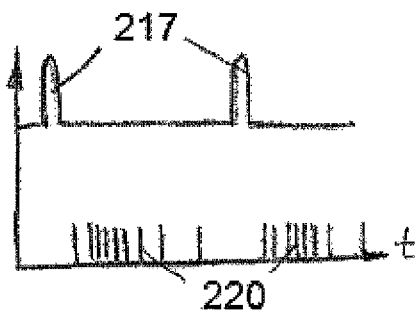
FIG. 20—these timing diagrams illustrate and alternative method of time-resolved fluorescence detection using a single-photon counter.

For time-resolved measurements, it is especially advantageous to use a single-photon counting detector. Then, instead of continuous response curve 218 as on FIG. 19, a number of pulses 220 would be detected, as depicted on FIG. 20. Statistical analysis of their time of arrival can provide the most accurate information about fluorescence-lifetime and/or the depth of fluorescent sources in the body.

It may also be possible to use multiple excitation lasers emitting short pulses within the same pixels and using the same detector to read multiple fluorophores. In this case, preferably, the fluorophores should have fairly short life time.

Additionally, the reflected light from one or more excitation lasers can be detected and co-processed with fluorescent light, thus enhancing the collected image.

Figure 21:
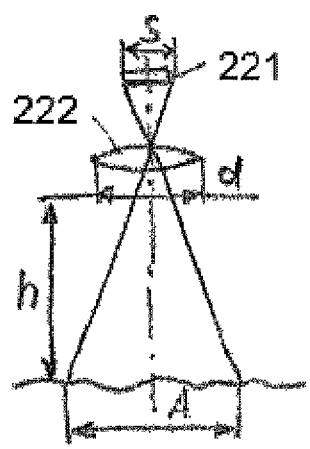
FIG. 21—this drawing illustrates the optical collection area trade-off between imaging and non-imaging detectors.

It is hence advantageous to use fast, highly sensitive detectors, such as Avalanche Photo-Diode (APD), Silicon Photo-Multiplier (SiPM), Photo-Multiplier Tube (PMT) Hybrid Photo-Multiplier (HPM) or other, characterized by short response time, high gain and low noise. It is also advantageous to use detectors with large active area, as those may collect more photons. Additionally, the size of optical collection area 222 may grow proportionally to the active area of the detector 221, so that $$d \approx 1 \ldots 2 * \frac{h*s}{A},$$

where d is the size of the optical collection area, S is the size of the active area of the detector, A is the size of the target, and h is the distance from the device to the target, as per FIG. 21.

Figure 22:
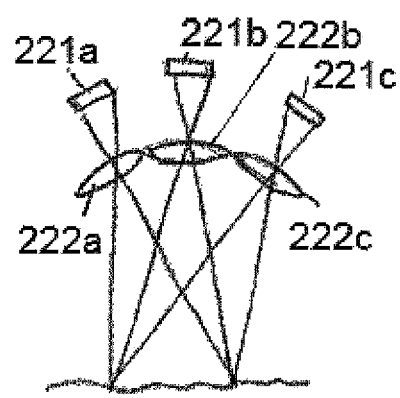
FIG. 22—this drawing shows multiple detectors with independent collection areas covering the same FOV.

Additionally, it may also be advantageous to employ multiple detectors 221a . . . 221c, each with its own optical collection area 222a . . . 222c, looking at the same target area (FIG. 22).

After both fluorescent image and color image are captured and aligned, various image fusion methods can be employed.

It may be particularly advantageous to capture the image formed by reflected excitation light in addition to the fluorescent image. The reflected image is usually providing more detailed, higher resolution information about the location of the fluorescent inclusions, while also being perfectly aligned with fluorescent image. The image data from the camera can then be used to colorize the reflected image, which otherwise is black-and-white.

It may also be advantageous to co-process the fluorescent and reflected image, for example, normalizing the fluorescent data by reflected data.

Also, additional information may be extracted from the analysis of temporal changes of the fluorescent images such as the direction and velocity of the blood flow, the pulse or other physiological factors. The contrast and quality of the fluorescent image can also be improved by storing the image taken before the fluorophore has been injected and comparing it with the image after the fluorophore injection.

This invention claims:

1. A fluorescence imaging device for detecting fluorescence in biological tissues and projecting a representative three-dimensional image onto the biological tissues, comprising:
   (a) a source of excitation light at an excitation wavelength, and means of delivering said excitation light to the biological tissues containing fluorescent substances;
   (b) a light collection system comprising a light detector configured to detect light emitted by the fluorescent substances at an emitted wavelength;
   (c) means of analyzing said detected light and establishing a three-dimensional spatial distribution of intensity of said light emitted by the fluorescent substances in the biological tissues;
   (d) means of generating a three-dimensional image representative of said three-dimensional spatial distribution of light intensity emitted by the fluorescent substances; and
   (e) means of projecting said three-dimensional representative image onto the biological tissues using a human-visible wavelength.

2. The fluorescence imaging device of claim 1 further comprising a source of ablation light and a processing unit configured to controllably deliver said ablation light to the imaged fluorescent substances, using said means of delivering.

3. The fluorescence imaging device of claim 1 wherein said source of excitation light comprises one or more lasers, and wherein said means of delivering said excitation light is configured for scanning said excitation light in a raster pattern onto an outer surface of the biological tissues.

4. The fluorescence imaging device of claim 3 wherein said light collection system comprises a filter configured to pass only said light emitted by the fluorescent substances at said emitted wavelength.

5. The fluorescence imaging device of claim 3,
   wherein said light detector comprises a scanning fluorescence detector configured to perform time domain analysis of multiple light emissions within the emitted light to distinguish fast-decaying fluorescent substances and slow-decaying florescent substances, each having identical emission spectra; and
   wherein said fluorescent imaging device further comprises a processing unit configured to drive said one or more lasers for said excitation light to be modulated to increase time resolution, said one or more lasers driven to modulate to emit pulses of a duration less than a duration of a scanned pixel.

6. The fluorescence imaging device of claim 3 wherein said detector is from the group of detectors consisting of:
   (a) a photo-diode (PD);
   (b) a avalanche photo-diode (APD);
   (c) a photo-multiplier tube (PMT);
   (d) a hybrid photo-multiplier (HPM); and
   (e) a silicon photo-multiplier (SiPM).

7. The fluorescence imaging device of claim 3 further comprising a plurality of said light detectors, each configured to detect said emitted light, with said emitted light being at the same wavelength.

8. The fluorescence imaging device of claim 3 wherein the excitation light is delivered at a plurality of wavelengths configured to excite a plurality of different fluorescent substances in the biological tissues, for the fluorescent substances to emit a plurality of different wavelengths.

9. The fluorescence imaging device of claim 8 further comprising a plurality of said light detectors configured to respectively detect said plurality of different emitted wavelengths from the fluorescent substances.

10. The fluorescence imaging device of claim 3 wherein said excitation wavelength does not match the maximum absorption of the fluorescent substances in the biological tissues.

11. The fluorescence imaging device of claim 3 wherein the emitted wavelength of light comprises a wavelength that is not visible to the human eye.

12. The fluorescence imaging device of claim 3 where one or both of the excitation light and said emitted light is NIR light with said emitted wavelength between 700 nm and 1000 nm.

13. The fluorescence imaging device of claim 3 where said three-dimensional image representative of said spatial distribution is projected using a source of visible light projected onto the biological tissues using said means of delivering.

14. The fluorescence imaging device of claim 3 further comprising: a processing unit; and means for capturing an image of the biological tissues in a human-visible spectrum having a field of view with an area being substantially the same as an area covered by said raster pattern of said scanned excitation light; and wherein said processing unit is configured to overlap said visible image of the biological tissues with said three-dimensional representative image of said spatial distribution of light intensity emitted by the fluorescent substances, and to display said overlapped images on a monitor.

15. The fluorescence imaging device of claim 5 further comprising a pixelated 2D image detector configured to capture one or more images of the biological area in a human-visible spectrum having a field of view with an area being substantially the same as an area covered by said raster pattern of said scanned excitation light; and wherein said processing unit is configured to overlap said visible image of the biological tissues with said three-dimensional representative image of said spatial distribution of light intensity emitted by the fluorescent substances, and to display said overlapped images on a monitor.

16. The fluorescence imaging device of claim 14, where said field of view (FOV) of said means for capturing an image is coaxially aligned by optical means with said area covered by said raster pattern of said scanned excitation light.

17. The fluorescence imaging device of claim 15, where said field of view of said pixelated 2D image detector is coaxially aligned with said area covered by said raster pattern using an optical device.

18. The fluorescence imaging device of claim 17, where said optical device is from the group of optical devices consisting of: one or more dichroic mirrors; one or more polarizing mirrors; and one or more semi-transparent mirrors.

19. The fluorescence imaging device of claim 17, where said pixelated 2D image detector is from the group of pixelated 2D image detectors consisting of a CCD camera; and a CMOS camera.

20. The fluorescence imaging device of claim 15, where said field of view (FOV) of said pixelated 2D image detector and said area covered by said raster pattern of said scanned excitation light are partially aligned by optical means.

21. The fluorescence imaging device of claim 18, where said field of view of said camera and said area covered by said raster pattern of said scanned excitation light are partially aligned with a bounce mirror for said raster pattern just outside of the camera FOV.

22. The fluorescence imaging device of claim 18, where said field of view of said camera and said area covered by said raster pattern of said scanned excitation light are partially aligned with a bounce mirror for said camera just outside of the FOV of said raster pattern.

23. The fluorescence imaging device of claim 18, where a frame rate of said scanned raster pattern and a frame rate of said camera are synchronized.

24. The fluorescence imaging device of claim 23, where said camera is configured to capture images in between said modulated pulses of said one or more lasers.

25. The fluorescence imaging device of claim 23, where said camera is configured to capture images in two separate streams comprising: a first stream of images captured in between said modulated pulses of said one or more lasers, and a second stream of images captured during said pulses of said one or more lasers.

26. The fluorescence imaging device of claim 25, where said processing unit is configured to compare said first and second streams and to extract alignment information to align said overlapped images.

27. The fluorescence imaging device of claim 5 where said pulses are shorter in duration than a duration of light collection for a single acquired pixel.

28. The fluorescence imaging device of claim 27 where a temporal distribution of fluorescent light in response to said short pulses is analyzed.

29. The fluorescence imaging device of claim 28 where the emitted light is detected by a single photon counter.

30. The fluorescence imaging device of claim 27 where said one or more lasers for said excitation light comprises a plurality of different lasers configured for said light to be delivered in a sequence of short pulses.

31. The fluorescence imaging device of claim 27 where information about a depth of the fluorescent substance in the biological tissue is extracted from a time delay between an emission of an excitation pulse and an arrival of the emission pulse.

32. The fluorescence imaging device of claim 27, where said one or more lasers for said excitation light is on for a first part of each pixel and is off for a second part of each pixel, and where said spatial distribution of light intensity emitted by the fluorescent substances collected during the second part is subtracted from said spatial distribution of light intensity collected during the first part to cancel out signals from non-fluorescent ambient light.

33. The fluorescence imaging device of claim 1 where said three-dimensional image representative of said spatial distribution of light intensity emitted by the fluorescent substances is enhanced by time variations of a brightness of various areas of said image.

34. The fluorescence imaging device of claim 1 where said three-dimensional image representative of said spatial distribution of light intensity emitted by the fluorescent substances is enhanced by indication of temporal changes in said three-dimensional spatial distribution of light.

35. The fluorescence imaging device of claim 1 where a bit resolution of said three-dimensional image representative of said three-dimensional spatial distribution of light intensity emitted by the fluorescent substances is automatically adjusted to optimize a contrast and reduce visible noise.

36. The fluorescence imaging device of claim 1 where a dynamic range image representative of said three-dimensional spatial distribution of light intensity emitted by the fluorescent substances is automatically adjusted to be always above the noise floor.

37. The fluorescence imaging device of claim 1 where multiple fluorescent images are averaged out to form the projected image with a lower level of noise.

38. The fluorescence imaging device of claim 1 where a bandwidth of the projected image is automatically adjusted to reduce a level of noise.

39. The fluorescence imaging device of claim 1 where polarized light is used for said means of projecting said image onto the biological tissues using said human-visible wavelength.

40. The fluorescence imaging device of claim 1 where said means of projecting is also used for general illumination of the biological tissues.

41. The fluorescence imaging device of claim 1 where an acquisition of said three-dimensional image representative of said three-dimensional spatial distribution of light intensity emitted by the fluorescent substances and said projection of said image are separated in time.

42. The fluorescence imaging device of claim 1 configured to acquire said three-dimensional image representative of said three-dimensional spatial distribution of light intensity emitted by the fluorescent substances of the 3D biological tissues, to project said three-dimensional image on one or more curved surfaces of the same biological tissues, to acquire a visible image of the same biological tissues, including at least part of said projected image, to co-analyze the acquired image representative of said three-dimensional spatial distribution of light intensity emitted by the fluorescent substances and the acquired visible image, and to apply adjustments to said projected image to ensure an accurate positional match therebetween.

43. The fluorescence imaging device of claim 1 where an intensity of said excitation light spatially varies depending on an intensity of said three-dimensional image representative of said three-dimensional spatial distribution of light intensity emitted by the fluorescent substances.

44. A device for acquiring a three-dimensional image of targeted biological tissues from fluorescent light emitted by fluorophores contained therein, and for projecting a three-dimensional visible representation of the acquired image onto the targeted biological tissues, said device comprising:

a first laser configured to emit a beam of visible light;
a second laser configured to emit a beam of fluorescence excitation light at an excitation wavelength to cause emission by the fluorophores of an emitted wavelength of light;
means for coaxially aligning the beams of visible light and fluorescence excitation light;
means for scanning the coaxially aligned light beams in a pattern onto the targeted biological tissues;
a processing unit configured to drive said second laser to emit two or more pulses of the fluorescence excitation light within a duration less than a duration of each of a plurality of pixels scanned by said means for scanning;
a scanning fluorescence detector configured to synchronously collect two or more corresponding pulses of light emitted by the fluorophores, within each of said scanned pixels; said scanning fluorescence detector further configured to perform time domain analysis of multiple light emissions within the emitted light to distinguish fast-decaying fluorescent substances and slow-decaying florescent substances, each having identical emission spectra;
wherein said processing unit is further configured to analyze the collected light to determine a depth of the fluorophores in the targeted biological tissues for each of said scanned pixels to establish a three-dimensional intensity distribution of the light emitted by the fluorophores; said processing unit further configured to generate a three-dimensional image representative of the spatial distribution; and
wherein said first laser is configured to receive the representative three-dimensional image, and to project the three-dimensional image, using said means for scanning, onto the one or more outer surfaces of the targeted biological tissues to overlay and align with the spatial distribution of light emitted by the fluorophores.

45. The device according to claim 44 further comprising a source of ablation light; and wherein said processing unit is further configured to controllably deliver said ablation light to the imaged fluorophores, using said means for coaxially aligning and said means for scanning.

46. The device according to claim 44 further comprising a pixelated 2D image detector configured to capture one or more images of the targeted biological tissues in a human-visible spectrum having a field of view substantially the same as an area covered by said pattern of said scanned light beams; and wherein said processing unit is configured to overlap said visible image of the biological tissues with the three-dimensional image representative of the spatial distribution, and to display said overlapped images on a monitor.

47. The device according to claim 46 further comprising an optical device configured to coaxially align the field of view of said pixelated 2D image detector with the area covered by said scanned pattern.

48. The device according to claim 47 wherein said optical device is from the group of optical devices consisting of: one or more dichroic mirrors; one or more polarizing mirrors; and one or more semi-transparent mirrors.

49. The device of claim 48, where said pixelated 2D image detector is from the group of pixelated 2D image detectors consisting of a CCD camera; and a CMOS camera.

50. The device according to claim 44 wherein the fluorescence excitation light and the emitted light is at a wavelength between 700 nm and 1000 nm.

51. The device according to claim 44 wherein the depth of the fluorophores is determined from a time delay between at least one of said pulses of fluorescence excitation light from said first laser and arrival of the corresponding pulse of light emitted by the fluorophores.

* * * * *